United States Patent [19] [11] 4,118,468
Strecker et al. [45] Oct. 3, 1978

[54] TECHNETIUM-99M-LABELLED DIAGNOSTIC AGENT FOR KIDNEY SCANNING AND PROCESS FOR ITS MANUFACTURE

[75] Inventors: Helmut Strecker, Seeheim; Reinhard Käsmarker, Hofheim; Gerhard Kloss, Kelkheim, all of Fed. Rep. of Germany

[73] Assignee: Hoechst Aktiengesellschaft, Frankfurt am Main, Fed. Rep. of Germany

[21] Appl. No.: 741,397

[22] Filed: Nov. 12, 1976

[30] Foreign Application Priority Data

Nov. 15, 1975 [DE] Fed. Rep. of Germany ....... 2551480

[51] Int. Cl.$^2$ .................. A61K 29/00; A61K 43/00
[52] U.S. Cl. ................. 424/1; 260/559 AT; 424/9; 250/303; 422/61

[58] Field of Search ............... 424/1, 1.5, 9; 260/559 AT; 250/303; 23/259

[56] References Cited

U.S. PATENT DOCUMENTS

| | | |
|---|---|---|
| 3,137,627 | 6/1964 | Buckwalter et al. ......... 260/559 AT |
| 3,725,295 | 4/1973 | Eckelman et al. ............ 252/301.1 R |
| 3,740,418 | 6/1973 | Rajamani et al. .......................... 424/1 |
| 3,859,429 | 1/1975 | Elias .......................................... 424/1 |
| 3,985,768 | 10/1976 | Priestap et al. ............... 260/559 AT |

*Primary Examiner*—Benjamin R. Padgett
*Assistant Examiner*—Christine M. Nucker
*Attorney, Agent, or Firm*—Curtis, Morris & Safford

[57] ABSTRACT

A diagnostic agent for the visualization of the kidneys is disclosed as well as a process for its manufacture. The new agent consists of pyrrolidinomethyl-tetracycline in a buffer solution, a tin(II) salt and technetium-99m in physiological sodium chloride solution.

10 Claims, No Drawings

TECHNETIUM-99M-LABELLED DIAGNOSTIC AGENT FOR KIDNEY SCANNING AND PROCESS FOR ITS MANUFACTURE

The present invention relates to a technetium-99m-labeled diagnostic agent for kidney scanning and to a process for its manufacture.

Because of its favorable radiation energy of 140 Kev, its relatively short half-life comprising 6 hours and the absence of corpuscular radiation, technetium-99m is used in nuclear medicine for diagnostic purposes. To avoid redundant losses of radioactivity which occur in the transportation of the product from the manufacturer to the client, technetium-99m is generally obtained from a so-called nuclide generator (for example as described in German Offenlegungsschrift No. 2,236,565) directly in the hospital.

The use of the technetium-99m (as $NaTcO_4$ in 0.9% NaCl solution) obtained from a nuclide generator of the type described above directly for the medical diagnostics is restricted, mainly to the brain, thyroid and stomach scanning. For further examinations, generally organ-specific carrier substances for the technetium-99m have to be labeled with the said radionuclide. Carrier substances are, for example, particles which are used, depending on their size, for lung or for liver diagnostics respectively and pyrophosphate for the visualization of the skeleton.

These carrier substances are labeled generally after a reduction of the technetium-99m in the form of the reaction-inert pertechnetate to highly reactive lower oxidation stages (probably 4 or 5). The reduction can be carried out in an acid medium (e.g. with thiosulfate), in a neutral medium (essentially using tin (II)) and electrolytically. In the first case, the reaction solution has to be neutralized before injection. So, a so-called "kit consisting of several components" is obtained. The electrolytic reduction requires a complicated system of apparatuses.

The labeling with technetium-99m is carried out in the hospital to avoid losses of radioactivity caused by its decay. For this reason, a simple, rapid and safe process is expedient. As the preparation is generally injected, it must be sterile, pyrogen-free and non-toxic. The use of labeling kits is on the increase. They consist of instruments coordinated with each other and of inactive substances which in combination with the nuclide generator product, give an organ-specific diagnostic agent. An especially easy to use labeling kit is a so-called "labeling unit" (a kit consisting of one component): this is a collecting vial containing a combination of substances into which the generator product has but to be injected to give the diagnostic agent ready for use.

Frequently, such labeling units consist of a combination of an organ-specific carrier substance with a tin(II)-salt.

Suitable substances and kits for kidney diagnostics with technetium-99m are known, for example technetium-99m-iron-ascorbate (German Offenlegungsschrift No. 2,124,751), technetium-99m-iron-ascorbate-EDTA (U.S. Pat. No. 3,740,418), technetium-99m-iron-DTPA (U.S. Pat. No. 3,466,361), technetium-99m-tin-penicillamine (U.S. Pat. No. 3,749,913), technetium-99m-tin-dimercapto-succinic acid (German Offenlegungsschriften Nos. 2,423,167; 2,419,310), technetium-99m-tin-glucoheptonate (P. Hambright et al., Journal of Nucl. Med. 1974, pages 478 et seq.) and technetium-99m-tin-tetracycline (C.P. Fliegel et al., Nucl. Med., 1974, page 407 et seq. and M. K. Dewanjee et al., Journal of Nucl. Med. 1974, page 176 et seq.). A comparison between the most important technetium-99m kidney diagnostic agents is made by W. Richards et al., Journal of Nucl. Med., 1975, pages 357 et seq.).

In a publication made by Isommerz GmbH, Berlin, "Wissenschaftliche Tagungen der DDR, XI. Nuclearmedizinisches Symposion Reinhardsbrunn 1974," pages 91–95, M. Krüger et al. disclose a technetium-labeled pyrrolidinomethyl-tetracyclinehydrochloride for kidney scanning. However, these agents are manufactured under conditions which do not produce optimum results.

In the case of the known diagnostic agents for kidneys, either the enrichment in the kidneys is too low, or there is too much enrichment in the other organs, the unlabeled preparation or the labeled solution is not stable enough, or the labeling procedure is too complicated.

For the time being, mercury-197-labeled diuretics are extensively used besides the technetium-99m-labeled compounds. Compared to technetium-99m, the $\beta$-ray emitter mercury-197 having a half-life of 2.7 days, considerably increases the radiation dose administered to a patient.

It is the object of the invention to manufacture a new kidney diagnostic agent which overcomes the drawbacks of the known diagnostic agents.

The present invention provides a process for the manufacture of a diagnostic agent for the visualization of the kidneys which comprises mixing pyrrolidinomethyl-tetracycline (Rolytetracycline, hereinafter abbreviated to read PMT) in a buffer solution having a pH value ranging between 5.0 and 6.5 at first with tin(II)-salt in a molar ratio of 10 to 100, preferably 30 to 50, mols of PMT per gram atom of tin(II), and then with technetium-99m-pertechnetate in physiological sodium chloride solution to yield a pH value ranging between 4 and 8, preferably 6.5 and 7.5.

It is advantageous to adjust the pH ranges by adding from 0.8 to 1.2 mols of phosphate buffer per mol of PMT. As the tin(II)-salt, the chloride is preferred.

Advantageously, the PMT and the tin-salt are mixed in the buffer solution and stored or transported in a reaction vial as the labeling unit. For this purpose, the solution is lyophilised before the addition of the pertechnetate and advantageously kept under an adequate protective gas, for example nitrogen. Immediately before use, in the hospital, the pertechnetate solution obtained from the nuclide generator is added, advantageously in physiological sodium chloride solution.

The present invention also provides a diagnostic agent for visualization of the kidneys consisting of pyrrolidinomethyl-tetracycline in a phosphate buffer solution having a pH value between 4 and 8, preferably between 6.5 and 7.5, tin(II)-salt in a ratio of 10–100 mols of PMT per gram atom of tin(II) and technetium-99m in physiological sodium chloride solution.

The new kidney diagnostic agent has the following advantages:

(a) Compared to the mercury-197-labeled diuretics used, the radiation dose values are considerably lower.

(b) The preparation shows a marked kidney specificity.

(c) The preparation on the basis of a labeling unit is simple and safe.

(d) The labeling unit is durable for at least 1 year at room temperature.

(e) The injection solution is durable for at least 8 hours.

The following Examples serve to illustrate the invention:

EXAMPLE 1

200 mg of PMT are dissolved in 9.4 ml of 0.05 m phosphate buffer of pH 6.0 and 200 micrograms of $SnCl_2 \cdot 2H_2O$ in 0.6 ml of 0.1 N HCl are added. The two solutions are rinsed with nitrogen until free of oxygen to protect the tin(II)-salt. From 1–10 ml of $Na^{99m}TcO_4$-solution (0.9% NaCl) are added within 2 hours. The diagnostic agent has a pH value of 6.8. It should be injected within 8 hours.

EXAMPLE 2

20 g of PMT are dissolved in 940 ml of 0.05 m phosphate buffer of pH 6.0 and 200 mg of $SnCl_2 \cdot 2 H_2O$ are dissolved in 60 ml of 0.1 N HCl. The two solutions are cooled to about 5° C., rinsed with nitrogen until free of oxygen and mixed while stirring. After filtration under sterile conditions (pore size of the filter: 0.2 micrometer) and with the exclusion of oxygen, the solution mixture is filled in 1 ml portions into vials, then immediately frozen in liquid nitrogen and lyophilised. The vials are filled with nitrogen in the lyophilisation apparatus and sealed, thus providing a unit suitable for labeling.

In case of need, from 1–10 ml of $Na^{99m}TcO_4$-solution in 0.9% of NaCl are added to the above given unit. The diagnostic agent has a pH value of 6.8. It should be administered within 8 hours.

What is claimed is:

1. A method for making a diagnostic agent for visualization of the kidneys, which method comprises mixing a buffer solution of pyrrolidinomethyl-tetracycline, said solution having an initial pH between 5.0 and 6.5, with a tin (II)-salt in a molar ratio of 10 to 100 mols of pyrrolidinomethyl-tetracycline per gram atom of tin (II) to give a first mixture, and then combining said first mixture with technetium-99m pertechnate in physiological sodium chloride solution to yield a second mixture having a final pH from 4 to 8.

2. The method as in claim 1 wherein the molar ratio of pyrrolidinomethyl-tetracycline to tin (II) in said first mixture is 30 to 50 mols per gram atom of tin (II).

3. The method as in claim 1 wherein the final pH in said second mixture is from 6.5 to 7.5.

4. The method as in claim 1 wherein said buffer solution contains from 0.8 to 1.2 mols of phosphate buffer per mol of pyrrolidinomethyl-tetracycline.

5. The method as in claim 1 wherein said first mixture is lyophilized before being combined with said technetium-99m pertechnate.

6. The method as in claim 5 wherein the lyophilized first mixture is under an inert protective gas.

7. A diagnostic agent for visualization of the kidneys, said agent consisting of a mixture, having a pH from 6.5 to 7.5, of a buffer solution of pyrrolidinomethyl-tetracycline, a tin (II) salt in a ratio of 10 to 100 mols of pyrrolidinomethyl-tetracycline per gram atom of tin (II), and of a solution of a technetium-99m pertechnate in physiological sodium chloride solution.

8. A kit for preparing, by the addition thereto of a physiological sodium chloride solution of technetium-99 m pertechnate, a diagnostic for visualization of the kidneys, said kit comprising a contained mixture of a tin (II) salt with a buffer solution of pyrrolidinomethyl-tetracycline having an initial pH from 5.0 to 6.5, said mixture containing 10 to 100 mols of pyrrolidinomethyl-tetracycline per gram atom of tin (II).

9. A kit as in claim 8 wherein said contained mixture is lyophilized.

10. A kit as in claim 9 wherein said lyophilized contained mixture is under an inert protective gas.

* * * * *